United States Patent
Auslender et al.

(10) Patent No.: US 8,283,925 B2
(45) Date of Patent: Oct. 9, 2012

(54) MAGNETIC RESONANCE METHOD AND APPARATUS TO REDUCE DISTORTIONS IN DIFFUSION IMAGING

(75) Inventors: Karin Auslender, Biel (CH); Thorsten Feiweier, Poxdorf (DE); Stefan Huwer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 409 days.

(21) Appl. No.: 12/650,757

(22) Filed: Dec. 31, 2009

(65) Prior Publication Data
US 2010/0171498 A1 Jul. 8, 2010

(30) Foreign Application Priority Data
Jan. 2, 2009 (DE) ......................... 10 2009 003 889

(51) Int. Cl.
*G01V 3/00* (2006.01)
(52) U.S. Cl. ....................................................... 324/309
(58) Field of Classification Search .......... 324/300–322; 600/410–435; 382/100–154
See application file for complete search history.

(56) References Cited

U.S. PATENT DOCUMENTS

| | | | |
|---|---|---|---|
| 5,864,233 A | 1/1999 | Zhou et al. | |
| 6,724,190 B2 * | 4/2004 | van Muiswinkel et al. | .. 324/307 |
| 7,057,388 B2 * | 6/2006 | Harvey et al. | ................. 324/309 |
| 7,218,110 B2 * | 5/2007 | Zhang et al. | ................... 324/309 |
| 7,902,825 B2 * | 3/2011 | Bammer et al. | ............. 324/309 |
| 2007/0223832 A1 | 9/2007 | Matsumoto | |

OTHER PUBLICATIONS

"Correction for Distortion of Echo-Planar Images Used to Calculate the Apparent Diffusion Coefficient," Ilaselgrove et al., Magnetic Resonance in Medicine, vol. 38 (1996) pp. 960-964.
"Eddy Currents Correction in Diffusion-Weighted Imaging Using Pairs of Images Acquired with Opposite Diffusion Gradient Polarity," Bodarnmer et al., Magnetic Resonance in Medicine, vol. 51 (2004) pp. 188-193.
Rapid Eddy Current Calibration and Prospective Distortion Correction Methods for Diffusion-Weighted BMI, Zaitsev et al., Proc. Intl. Soc. Mag. Reson. Med., vol. 13 (2005) p. 502.

* cited by examiner

*Primary Examiner* — Dixomara Vargas
(74) *Attorney, Agent, or Firm* — Schiff Hardin LLP

(57) ABSTRACT

In a method and magnetic resonance (MR) system for correction of image distortions that occur in acquisitions of diffusion-weighted MR images of an examination subject a first adjustment measurement with a first diffusion weighting is implemented, a second adjustment measurement with a second diffusion weighting is implemented and correction parameters to de-skew diffusion-weighted MR images are automatically calculated in a computer on the basis of the two adjustment measurements. One of the two adjustment measurements is implemented with a predetermined diffusion weighting in three orthogonal diffusion directions, and correction parameters are determined for the three orthogonal diffusion directions.

16 Claims, 3 Drawing Sheets

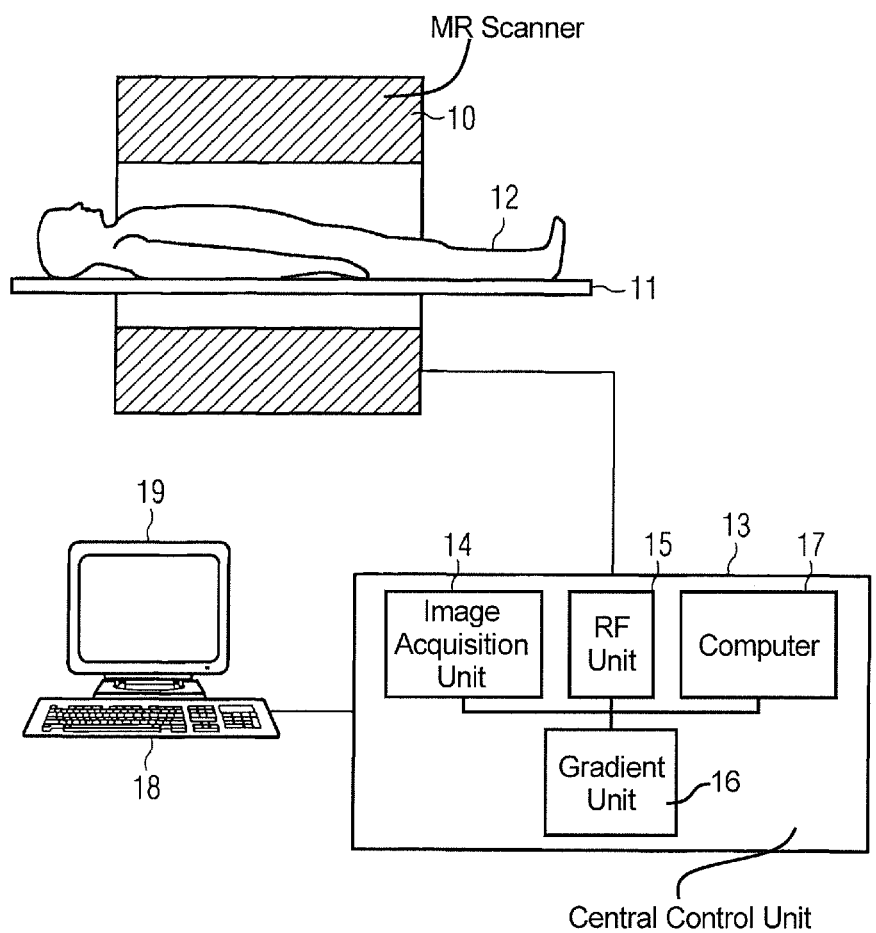

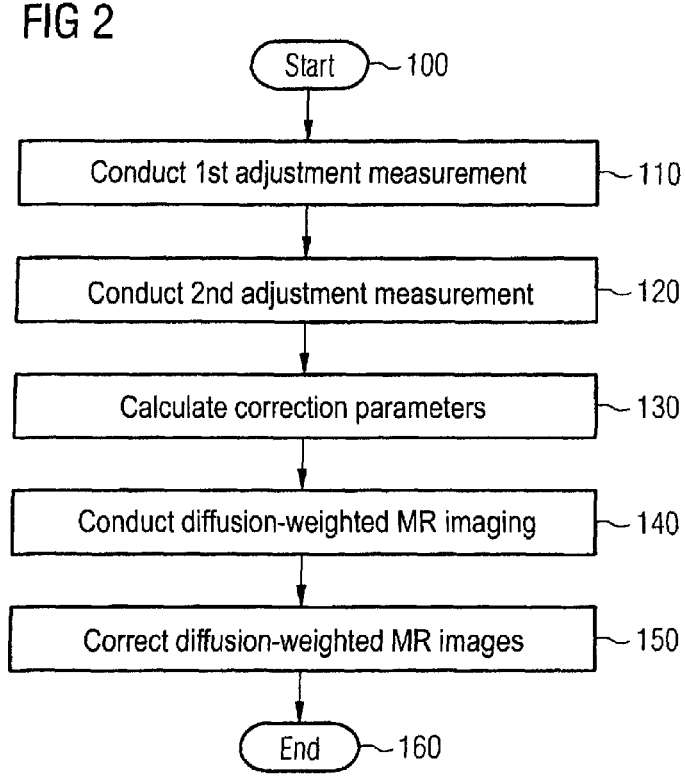

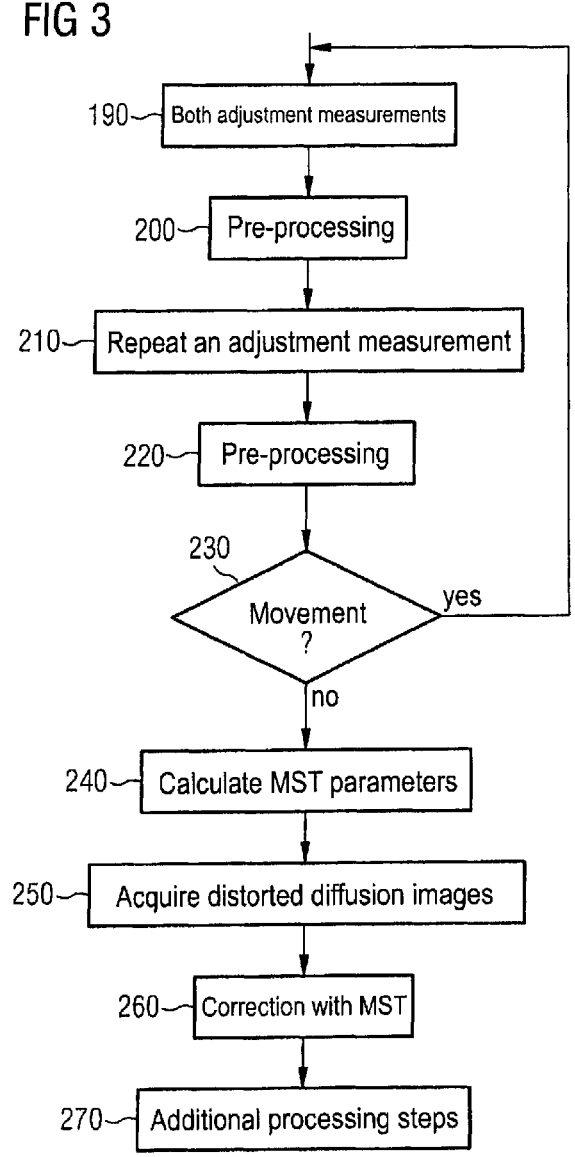

MAGNETIC RESONANCE METHOD AND APPARATUS TO REDUCE DISTORTIONS IN DIFFUSION IMAGING

BACKGROUND OF THE INVENTION

1. Field of the Invention

The invention concerns a method for the correction of image distortions that occur in exposures of diffusion-weighted magnetic resonance images (MR images) of an examination subject, as well as a magnetic resonance system (MR system) for this. The invention is in particular applied in the correction of diffusion-weighted images that were acquired using the echoplanar technique (EPI).

2. Description of the Prior Art

In echoplanar imaging, after a single RF excitation pulse with a series of echoes in the readout gradients signals are generated that can be associated with different lines in k-space by a modulation of the phase coding gradients. Distortions due to eddy currents represent a great challenge in diffusion-weighted EPI imaging since high gradient amplitudes for diffusion imaging (known as the diffusion gradients) are used in combination with a high sensitivity in the phase coding direction, which leads to the distortions. In the phase coding direction, the resolution in such EPI images is typically approximately 10 Hz per pixel.

In diffusion imaging, generally multiple MR images with different diffusion directions and diffusion weightings are acquired and combined with one another in order to calculate parameter maps for diffusion coefficients, for example, such as ADC (Apparent Diffusion Coefficient) or FA (Fractional Anisotropy). The diffusion weighting is described by a b-value that depends on the strength of the applied diffusion gradient and is measured in seconds per square millimeter. These diffusion images with different diffusion directions and weightings can then be used for diagnostic purposes. The eddy current fields that are generated by the diffusion gradients, however, lead to image distortions whose appearance depends both on the amplitude of the gradients (i.e. the diffusion weighting) and on their direction. The distortions can be described in a good approximation as a simple affine transformation with the scaling M, the shear S and the displacement or translation T. If the acquired individual images are combined with one another without correction, the different distortions for each image lead to incorrect associations of pixel information, and therefore to errors or at least to a reduced precision of the calculated parameters.

In the prior art, several image-based methods are known for the correction of eddy current-based distortions in diffusion imaging. For example, it is described in Haselgrove et al. in MRM 36:960-964, 1996 that an MR image with b=0 (i.e. an undistorted image) is acquired which serves as a reference image. Furthermore, an additional adjustment measurement with lower diffusion weighting is acquired for the direction to be corrected, wherein a low diffusion weighting means, for example, a b-value of 150 s/mm$^2$. The distortion parameters M, S and T determined with these measurements are utilized using an extrapolation relationship for the correction of the actual diffusion-weighted MR images in which the b-value is, for example, 1000 s/mm$^2$.

This method has the disadvantage that an adjustment measurement is necessary for every diffusion direction. For a precise conclusion about the diffusion, however, information is also required in a great many different directions, for example between 5 and 200 different directions. Since an adjustment measurement is necessary for every diffusion direction, this would lead to intolerably long acquisition times. In diffusion-weighted images with b=150 s/mm$^2$, the distortions are not yet very strongly pronounced, such that the precise determination of the parameters such as scaling, shearing and translation is difficult. Via the extrapolation of these values to larger b-values, errors in the determination of the b150 MR image are intensified. Movements between the acquisition of the reference image and the adjustment measurement can likewise lead to incorrect determination of the correction parameters. Furthermore, the contrast between the two images is very similar but not identical, which leads to an inadequate robustness of the method as soon as tissue with rapidly diffusing water molecules is present in the image.

Furthermore, in Bodammer et al. in MRM 51:188-193, 2004 it is described that two images with identical diffusion direction and weighting but inverted polarity are acquired. While the diffusion contrast remains unchanged given inverted polarity, the inversion affects the distortion by a compression being produced from a stretching, a negative shear is produced from a positive shear and a negative translation is produced from a positive translation. In this method, two images must be acquired for each diffusion direction and for every diffusion weighting. Moreover, the signal-to-noise ratio in images with high b-values can be extremely high, which makes the precise determination of the correction parameters difficult. Furthermore, contrast differences due to directed movement (for example flow or pulsations) can lead to an inadequate robustness of the method. Furthermore, movements between the acquisition of the two measurements can lead to incorrect determinations of the correction parameters.

SUMMARY OF THE INVENTION

An object of the present invention is to provide an improved correction method for image distortions in the acquisition of diffusion-weighted MR images.

This object is achieved via the features of the independent Claims. Preferred embodiments of the invention are described in the dependent Claims.

According to a first aspect of the invention, a method is provided in which a first adjustment measurement is implemented with a first diffusion weighting and a second adjustment measurement is implemented with a second diffusion weighting. As used herein, an "adjustment measurement" is a magnetic resonance dataset that is not used for reconstruction of a magnetic resonance image that is intended for use in making the actual medical diagnosis. The actual diagnostic magnetic resonance image is subsequently obtained and corrected based on the adjustment magnetic resonance datasets. Such correction parameters are calculated to de-skew the diffusion-weighted MR images on the basis of the two adjustment measurements. One of the two adjustment measurements is fashioned to be implemented with a predetermined diffusion weighting in three orthogonal diffusion directions. Correction parameters for the three orthogonal diffusion directions are additionally determined. According to the invention, one of the two adjustment measurements is implemented only with one diffusion weighting and only with three orthogonal diffusion directions. A linearity of the amplitudes of the distortions and an independent linear superposition of the orthogonal eddy current fields is hereby assumed. The correction parameters for diffusion-weighted MR images with arbitrary diffusion direction are advantageously defined by linear combination from the correction parameters for the three orthogonal diffusion directions. For example, if the distortion parameters for the x-direction (1,0,0), the y-direction (0,1,0) and the z-direction (0,0,1) are known, the correction parameters required for the direction (X,Y,Z)=x·(1,0,0)+ y·(0,1,0)+z·(0,0,1) can be directly determined, whereby the measurement time is significantly reduced. Every arbitrary diffusion direction, or the correction parameters for MR images with this diffusion direction, can be calculated by a linear combination of the correction parameters that are determined for the three orthogonal diffusion directions. Instead of adjustment measurements in 5 to 200 different directions, only measurements in three orthogonal diffusion directions are necessary. If adjustment measurements with a different diffusion weighting from the MR images to be corrected are employed, an extrapolation or interpolation of the correction parameters can be additionally conducted.

The three orthogonal diffusion directions advantageously correspond to the directions of the three magnetic field gradients that are used in the acquisition of the diffusion-weighted MR images.

According to a further embodiment of the invention, in one of the two adjustment measurements a diffusion weighting with a diffusion factor b is applied that lies between 200 and 800 s/mm², for example at 500 s/mm². This is a b-value that first guarantees a sufficient signal-to-noise for a precise determination of the parameters and second already generates sufficiently strong distortions, which likewise positively affects the precision.

According to a further embodiment of the invention, the movement of the examination subject between the adjustment measurements is detected, wherein the correction parameters for the de-skewing are used for the de-skewing of diffusion-weighted MR images only if the movement is less than a predetermined limit value. This can mean that adjustment measurements are repeated given detection of movement amplitudes above the limit value. In a simple case, for example, each adjustment measurement (and possibly the reference measurement) can be implemented multiple times, and these images are successively compared with one another. If the comparison shows a correlation of the images that is too low, this is interpreted as a movement, and the adjustment measurement can be repeated until the correction parameters can be determined free of movement artifacts. With the minimized scope of the necessary adjustment measurements according to the invention, it is foremost that the risk of a movement due to the short acquisition time is reduced, and second that the temporal disadvantage given a necessary repetition of the adjustment measurement can be kept small.

According to a preferred embodiment, the movement between the adjustment measurements is determined via calculation of an entropy measure. An entropy measure—for example "Normalized Mutual Information" (NMI)—has the advantage that it does not depend on the contrast of the acquired images.

Furthermore, only signal intensities in the respective MR images that are greater than a predetermined threshold can be taken into account in the calculation of the correction parameters from the adjustment measurements. For example, the similarity assessment of two images can be limited to the information-bearing portions of the image with such a noise detection. For example, the one or the other adjustment measurement can be used to generate a mask, wherein only image intensities above the threshold are used. This predetermined threshold can be hard-set or be dynamically determined from the image information.

Before the calculation of the correction parameters, an edge detection filter can likewise be applied to the MR images as pre-processing in order to subsequently calculate the correction parameters using the filtered image data. Through consideration in particular of the edges in the diffusion-weighted MR images, it is possible to more simply and quickly detect distortions in the MR diffusion image (such as translation, shear or enlargement or, respectively, reduction) independent of the signal intensity.

In a further embodiment, in the calculation of the correction parameters for translation, scaling and shear optimization methods can be used in which the entirety of the image information is simultaneously taken into account to calculate the correction parameters. In the two methods of the prior art according to Bodammer and Haselgrove, the images are compared with one another line by line to calculate the correction parameters, and the complete reasonable parameter space is evaluated in a "brute force" approach in order to determine the optimal parameter set for translation, shear and enlargement/reduction. In the embodiment proposed here, the complete adjustment image is subjected step by step to an MST transformation and the similarity comparison is implemented on the entire image, and not line by line. Although the individual steps require longer calculation times, the number of steps can be significantly reduced so that the entire calculation time remains within the boundaries. Furthermore, the use of the entirety of the image information has the advantage of using better similarity measures than the cross-correlation, for example the aforementioned Normalized Mutual Information (NMI). Furthermore, here the limitation to an established precision or, respectively, increment of the correction parameters is foregone. For example, a simplex optimization method can be used since it merely requires function values and not gradients and is also for the most part in the position to find a global minimum in an optimization space with local minima.

The invention furthermore concerns an MR system to acquire the diffusion-weighted MR images, with an image acquisition unit to acquire the diffusion-weighted MR images and the adjustment measurements with the different diffusion weightings. A computer is likewise provided that calculates the correction parameters to de-skew the diffusion-weighted MR images on the basis of the two adjustment measurements. The image acquisition unit implements a diffusion weighting in three orthogonal diffusion directions in one or the two adjustment measurements. The computer determines the correction parameters for the three orthogonal diffusion directions. The MR system (in particular the computer) operates as described in detail above.

The method described here for the improvement of the correction of image distortions can be applied both to the method described by Bodammer et al. and to the method described by Haselgrove et al. In the method described by Haselgrove, the first adjustment measurement corresponds to the first diffusion weighting of the reference measurement without diffusion gradient. In this case, this means that the first diffusion weighting would be zero. The second adjustment measurement is then implemented in the three orthogonal diffusion directions with the predetermined diffusion weighting. Given the application of the method according to the invention to the method from Bodammer et al., the first adjustment measurement with the first diffusion weighting would be the negative diffusion weighting while the second adjustment measurement would be the measurement with the same positive diffusion weighting.

BRIEF DESCRIPTION OF THE DRAWINGS

FIG. 1 schematically illustrates an MR system with which distortions in diffusion-weighted MR images can be corrected in accordance with the invention.

FIG. 2 is a flowchart with the basic steps for correction of distortions in accordance with the invention.

FIG. 3 is a flowchart of a further embodiment for the correction of distortions in MR diffusion imaging in accordance with the invention.

DESCRIPTION OF THE PREFERRED EMBODIMENTS

In FIG. 1 an MR system is shown with which diffusion-weighted MR images can be acquired with the aid of the echoplanar technique and with which distortions in the diffusion images that are due to eddy currents can be reduced. The MR system has a scanner 10 with a basic field magnet into which an examination subject 12 on a bed 11 is moved in order to acquire MR images of the examination subject 12 in the center of the scanner 10. The MR system furthermore has a central control unit 13 that is used to control the MR scanner 10. The central control unit 13 has an image acquisition unit 14 for pulse sequence control in which the sequence of the RF pulses and the sequence of the gradient switches are controlled depending on the selected imaging sequence. The generation of MR images by radiation of RF pulses and the generation of gradient fields is known to those skilled in the art and need not be explained in detail herein. The central control unit 13 furthermore has an RF unit 15 to control the RF pulses an a gradient unit 16 to control the magnetic field gradients that are switched during the imaging. In addition to the gradients for the spatial coding, diffusion gradients of different strengths are switched to create diffusion-weighted images. In the generation of diffusion-weighted MR images using the EPI technique, the images are distorted due to the low frequency differences in the phase coding direction. In particular, eddy currents lead to significant distortions in the phase coding direction. For example, a remaining gradient in the slice selection direction (z-direction) leads to a uniform translation of every pixel in the phase coding direction y given the acquisition of diffusion-weighted MR images with the EPI technique. A gradient in the frequency coding direction x generates a field changing linearly with x. Every column (i.e. every pixel) with a predetermined y-coordinate is hereby shifted linearly with x, which leads to a shear of the entire image parallel to the y-direction. A residual gradient in the phase coding direction y that leads to a linearly changing field depending on y means that every pixel is shifted in the y-direction by an amount that is linearly connected with the y-position. This means a size change, enlargement or reduction in the y-direction. This enlargement is independent of x.

As is described in detail in the prior art in Haselgrove et al. or Bodammer et al., correction parameters can be calculated for the translation T, for the shear S and for the enlargement/reduction M. For this purpose, in the device of FIG. 1 a computer 17 is provided that calculates from adjustment measurements (datasets) the correction parameters that are necessary to de-skew diffusion-weighted MR images with the EPI technique. Furthermore, an input unit 18 and a display unit 19 are provided with whose help the MR system can be operated by an operator and on which MR images can be displayed or, respectively, measurements can be planned.

The basic steps with which system-dependent distortions in diffusion-weighted MR images can be corrected are shown in FIG. 2. After the start of the method in Step 100, a first adjustment measurement is implemented in Step 110. Given the application of the present method to the method described in Haselgrove et al., the first adjustment measurement is a measurement a diffusion weighting of zero, i.e. with a value $b=0$ s/mm$^2$, whereby an undistorted MR image is obtained that serves as a reference for the calculation of the distortion of diffusion-weighted MR images with diffusion weighting $b\neq 0$ s/mm$^2$.

Given the application of the present method from Bodammer et al., the first adjustment measurement is a measurement with a predetermined diffusion weighting with negative polarity.

A second adjustment measurement is implemented in Step 120. Applied to the method from Bodammer et al., this second adjustment measurement is the measurement with the same diffusion weighting but positive polarity. Applied to the method of Haselgrove et al., the second adjustment measurement is an adjustment measurement with an average diffusion weighting with a b-value between 200 and 800 s/mm$^2$ (for example 500 s/mm$^2$) in order to obtain a certain distortion relative to the undistorted reference image, but the diffusion weighting is not selected so high so that the poor signal-to-noise ratio in measurements with high diffusion weighting does not unnecessarily make the subsequent calculation more difficult. In Step 130, the correction parameters for translation, shear or scaling (T, M and S) that can be used to correct diffusion-weighted MR images are then calculated. The adjustment measurements implemented in Steps 110 and 120 are assumed given application of the method to the method according to Bodammer et al. in three orthogonal spatial directions with negative polarity and with three orthogonal spatial directions with positive polarity. All other distortions at different diffusion weightings and directions can then be calculated from the distortions with negative polarity and the distortions with positive polarity. With the application of the method to Haselgrove et al., in Step 120 diffusion gradients in the three different spatial directions are measured only in the second adjustment measurement, and correction parameters M, S and T for this are calculated. Correction parameters for any arbitrary spatial direction can then be calculated via superposition or, respectively, linear combination. When diffusion-weighted diagnostic MR images are acquired in Step 140, this leads to distorted MR images, wherein the distortion depends on the strength and the direction of the applied diffusion gradient. The diffusion-weighted MR images can be corrected in Step 150, wherein this correction for any arbitrary diffusion direction and weighting is possible via superposition of the distortions in the three individual spatial directions and (possibly) extrapolation or interpolation of the correction parameters. The latter ensues, as described by Haselgrove, via scaling of the parameters with the ratio of the diffusion gradient amplitudes (i.e. with the ratio of the square root of the b-values). If the diffusion-weighted MR images are assumed with a defined diffusion direction, the distortions incurred for these images are calculated and the diffusion-weighted MR images are corrected. The method ends in Step 160.

An additional embodiment that shows additional details of the correction method under consideration of the movement correction is described in FIG. 3. After the implementation of the two adjustment measurements (Step 190) as described in FIG. 2, a pre-processing can optionally ensue in Step 200 as shown in FIG. 3. In this pre-processing, for example, the MR images from the adjustment measurements are pre-processed such that, before the calculation of the distortion parameters, with a noise detection only image regions with intensities above a predetermined threshold are considered. The contour of the examined region can likewise be intensified with an edge detection filter in order to calculate the shear, translation and enlargement or reduction using only the contour. The robustness of the method can be significantly improved via the changes implemented in this processing step 200. In the next Step 210, one of the two adjustment measurements is then repeated and—after a pre-processing repeated in Step 220 (similar to as in Step 200)—the repeated adjustment measurement is then compared with the corresponding measurement of Step 190 in order to check whether a movement has occurred between the examinations (Step 230).

Given the comparison of the repeated adjustment measurement with the corresponding adjustment measurement from Step 190, for example, a similarity measure such as the NMI can be used, wherein the NMI measure has the advantage that it is independent of the contrast in the generated MR images. If the degree of similarity in Step 230 between the pre-processed, repeated adjustment image and the pre-processed image of the corresponding first adjustment measurement is greater than a tolerance value, this means that the correlation measure is large enough in order to implement the transformation with regard to M, S and T in Step 240. However, if the degree of similarity is less than the tolerance value, the measurements must be repeated. The diffusion-weighted MR images that are distorted due to the diffusion weighting are then acquired in Step 250. These can be corrected in Step 260 with the parameters calculated in Step 240, whereby a diffusion-weighted MR image is obtained in which the distortion due to diffusion weighting is minimized. The MR images obtained in Step 260 can then be used as a basis for further processing steps 270.

With the minimized scope of the necessary adjustment measurement, the risk of the movement due to the short acquisition time period is reduced. Furthermore, the additional time cost given a necessary repetition due to the measurement in the three orthogonal spatial directions is relatively small.

In the event that this tolerance range was not complied with in Step 260, the correction parameters must be recreated in Step 270, meaning that the adjustment measurements must be repeated. If the entropy lies within the tolerance range, the final image and the final correction parameters can be identified in Step 280 and the final corrected diffusion image can be used to calculate the diffusion variables.

The method described in connection with FIG. 3 has the advantage that it is insensitive to movements, has a short measurement time overall due to the shorter adjustment measurements and operates robustly and reliably.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating a diffusion-weighted magnetic resonance image that is substantially free of image distortions, comprising the steps of:
   obtaining a first adjustment magnetic resonance dataset of an examination subject in a magnetic resonance data acquisition unit by implementing a magnetic resonance data acquisition sequence with a first diffusion weighting in said magnetic resonance data acquisition unit;
   obtaining a second adjustment magnetic resonance dataset of the examination subject in the magnetic resonance data acquisition unit by implementing a magnetic resonance data acquisition sequence with a second diffusion weighting in said magnetic resonance data acquisition unit;
   obtaining one of said first or second adjustment magnetic resonance datasets with a predetermined diffusion weighting in three orthogonal diffusion directions; and
   providing said first and second adjustment magnetic resonance datasets to a processor and, in said processor, automatically calculating correction parameters, in each of said three orthogonal diffusion directions that de-skew diffusion weighted magnetic resonance images, and making said correction parameters available at an output of said processor in a form allowing correction of a subsequently-obtained diffusion-weighted diagnostic magnetic resonance image with said correction parameters to substantially correct for image distortions arising due to the diffusion-weighting in said diagnostic magnetic resonance image.

2. A method as claimed in claim 1 comprising acquiring said diffusion-weighted diagnostic magnetic resonance image of the examination subject in said magnetic resonance data acquisition unit, and correcting said diffusion-weighted diagnostic magnetic resonance image using said correction parameters.

3. A method as claimed in claim 1 comprising, in said processor, generating correction parameters for diffusion-weighted magnetic resonance images in arbitrary diffusion directions by a linear combination of said correction parameters for said three orthogonal diffusion directions.

4. A method as claimed in claim 1 comprising acquiring said first and second adjustment magnetic resonance datasets by activating magnetic field gradients in each of three directions, and employing said three directions respectively as said three orthogonal diffusion directions.

5. A method as claimed in claim 1 comprising employing said predetermined diffusion weighting with a diffusion factor b in a range between 200 and 800 s/mm$^2$.

6. A method as claimed in claim 1 comprising employing said predetermined diffusion weighting with a diffusion factor b in a range between 400 and 600 s/mm$^2$.

7. A method as claimed in claim 1 comprising employing said predetermined diffusion weighting with a diffusion factor b of 500 s/mm$^2$.

8. A method as claimed in claim 1 comprising detecting physical movement of the examination subject while obtaining each of said first and second adjustment magnetic resonance datasets, and using said correction parameters to correct said subsequently acquired magnetic resonance diagnostic image of the examination subject only if the detected movement is less than a predetermined limit value.

9. A method as claimed in claim 8 comprising detecting said movement by comparing magnetic resonance images respectively reconstructed from said first and second adjustment magnetic resonance datasets, with a calculation of an entropy measure.

10. A method as claimed in claim 1 wherein each of said first and second magnetic resonance adjustment datasets represents pixels having respective intensities, and, for calculating said correction parameters, employing only pixels represented by said first and second magnetic resonance adjustment datasets that have an intensity that is larger than a predetermined intensity threshold.

11. A method as claimed in claim 1 comprising applying an edge detection filter to each of said first and second magnetic resonance adjustment datasets, to obtain first and second edge detection filtered datasets, and calculating said correction parameters from said first and second edge detection filtered datasets.

12. A method as claimed in claim 1 comprising calculating, as said correction parameters that de-skew diffusion-weighted magnetic resonance images, correction parameters respectively for translation, scaling and shear in an iterative calculation using all of said first and second adjustment magnetic resonance datasets.

13. A magnetic resonance apparatus for generating a diffusion-weighted magnetic resonance image that is substantially free of image distortions, comprising a magnetic resonance data acquisition unit;

a control unit is configured to operate said magnetic resonance data acquisition unit to obtain a first adjustment magnetic resonance dataset of an examination subject in the magnetic resonance data acquisition unit by implementing a magnetic resonance data acquisition sequence with a first diffusion weighting in said magnetic resonance data acquisition unit;

said control unit being configured to operate said magnetic resonance data acquisition unit to also obtain a second adjustment magnetic resonance dataset of the examination subject in the magnetic resonance data acquisition unit by implementing a magnetic resonance data acquisition sequence with a second diffusion weighting in said magnetic resonance data acquisition unit;

said control unit being configured to operate said magnetic resonance data acquisition unit to obtain one of said first or second adjustment magnetic resonance datasets with a predetermined diffusion weighting in three orthogonal diffusion directions; and a processor provided with said first and second adjustment magnetic resonance datasets, said processor being configured to automatically calculate correction parameters, in each of said three orthogonal diffusion directions that de-skew diffusion weighted magnetic resonance images, and to make said correction parameters available at an output of said processor in a form allowing correction of a subsequently-obtained diffusion-weighted diagnostic magnetic resonance image with said correction parameters to substantially correct for image distortions arising due to the diffusion-weighting in said diagnostic magnetic resonance image.

14. A magnetic resonance apparatus as claimed in claim 13 wherein said control unit is configured to operate said magnetic resonance data acquisition unit to acquire diagnostic magnetic resonance dataset reprinting said diffusion-weighted diagnostic magnetic resonance image of the examination subject, and said apparatus comprising a computer configured to reconstruct said diffusion-weighted magnetic resonance image from said diagnostic magnetic resonance dataset and to correct said diffusion-weighted diagnostic magnetic resonance image using said correction parameters.

15. A magnetic resonance apparatus as claimed in claim 13 wherein said processor is configured to generate correction parameters for diffusion-weighted magnetic resonance images with arbitrary diffusion directions by a linear combination of said correction parameters for said three orthogonal diffusion directions.

16. A magnetic resonance apparatus as claimed in claim 13 wherein said magnetic resonance data acquisition unit comprises a gradient coil system that generates gradient magnetic fields respectively in three orthogonal directions while obtaining said first and second adjustment magnetic resonance datasets, and wherein said processor employs said three orthogonal directions of said gradient magnetic fields as said three orthogonal diffusion directions.

\* \* \* \* \*